US011213573B2

(12) United States Patent
Raemdonck et al.

(10) Patent No.: US 11,213,573 B2
(45) Date of Patent: Jan. 4, 2022

(54) PARTICLES COMPRISING SURFACTANT PROTEIN B AND ONE OR MORE LIPIDS

(71) Applicants: Universiteit Gent, Ghent (BE); Universidad Complutense De Madrid, Madrid (ES)

(72) Inventors: Koen Raemdonck, Ghent (BE); Stefaan De Smedt, Mariakerke (BE); Jésus Pérez-Gil, Madrid (ES)

(73) Assignees: UNIVERSITEIT GENT, Ghent (BE); UNIVERSIDAD COMPLUTENSE DE MADRID, Madrid (ES)

( * ) Notice: Subject to any disclaimer, the term of this patent is extended or adjusted under 35 U.S.C. 154(b) by 0 days.

(21) Appl. No.: 16/463,946

(22) PCT Filed: Nov. 23, 2017

(86) PCT No.: PCT/EP2017/080263
§ 371 (c)(1),
(2) Date: May 24, 2019

(87) PCT Pub. No.: WO2018/096057
PCT Pub. Date: May 31, 2018

(65) Prior Publication Data

US 2020/0197496 A1 Jun. 25, 2020

(30) Foreign Application Priority Data

Nov. 24, 2016 (EP) .................................... 16200515

(51) Int. Cl.
*A61K 38/17* (2006.01)
*A61P 11/00* (2006.01)
*A61K 9/51* (2006.01)

(52) U.S. Cl.
CPC .......... *A61K 38/395* (2013.01); *A61K 9/5138* (2013.01); *A61K 9/5161* (2013.01); *A61P 11/00* (2018.01)

(58) Field of Classification Search
CPC .................................................... A61K 38/395
See application file for complete search history.

(56) References Cited

U.S. PATENT DOCUMENTS

2007/0238676 A1 10/2007 Mohapatra et al.

FOREIGN PATENT DOCUMENTS

| | | | |
|---|---|---|---|
| WO | 199630051 | A1 | 10/1996 |
| WO | 199939742 | A1 | 8/1999 |
| WO | 2013120058 | A2 | 8/2013 |
| WO | 2014079898 | A1 | 5/2014 |

OTHER PUBLICATIONS

De Backer et al., "The influence of natural pulmonary surfactant on the efficacy of siRNA-loaded dextran nanogels", Nanomedicine (2013) 8(10), 1625-1638 (Year: 2013).*

Blanco et al., "Biochemical and pharmacological differences between preparations of exogenous natural surfactant used to treat Respiratory Distress Syndrome: Role of the different components in an efficient pulmonary surfactant", European Journal of Pharmacology 568 (2007) 1-15 (Year: 2007).*

Poelma et al., "Distinct effects of SP-B and SP-C on the uptake of surfactant-like liposomes by alveolar cells in vivo and in vitro", Am J Physiol Lung Cell Mol Physiol 287: L1056-L1065, 2004. (Year: 2004).*

Guagliardo et al., "Surfactant Protein B Promotes Cytosolic SiRNA Delivery by Adopting a Virus-like Mechanism of Action", ACS Nano, published Mar. 16, 2021 (Year: 2021).*

European Search Report dated Jun. 8, 2017 in reference to EP 16200515.1, 10 pages.

International Search Report dated Mar. 29, 2018 in reference to PCT/EP2017/080263, 16 pages.

Karagiannis, et al., "Rational Design of a Biomimetic Cell Penetrating Peptide Library", ACS Nano 20131022 American Chemical Society USA, vol. 7, No. 10 Oct. 22, 2013, pp. 8616-8626.

Baatz, et al., "Utilization of Modified Surfactant-Associated Protein B for Delivery of DNA to Airway Cells in Culture", Proceedings National Academy of Sciences PNAS, National Academy of Sciences, US, vol. 91, No. 7 Mar. 1, 1994, pp. 2547-2551.

De Backer, L., et al., The Influence of Natural Pulmonary Surfactant on the Efficacy of Sirna Loaded Dextran Nanogels. Nanomedicine (London, United Kingdom), 2013. 8(10): p. 1625-1638.

De Backer, L., et al., Hybrid Pulmonary Surfactant-Coated Nanogels Mediate Efficient In Vivo Delivery of siRNA to Murine Alveolar Macrophages. Journal of Controlled Release, 2015. 217: p. 53-63.

Serrano, et al., "Protein-Lipid Interactions and Surface Activity in the Pulmonary Surfactant System", Chemistry and Physics of Lipids, Limerick, IR, vol. 141, No. 1-2, Jun. 1, 2006, pp. 105-118.

Blanco, et al., Biochemical and Pharmacological Differences Between Preparations of Exogenous Natural Surfactant Used to Treat Respiratory Distress Syndrome: Role of the Different Components in an Efficient Pulmonary Surfactant. European Journal of Pharmacology, 2007; 568: pp. 1-15.

De Backer, L., et al., Bio-Inspired Pulmonary Surfactant-Modified Nanogels: A Promising siRNA Delivery System. Journal of Controlled Release, 2015. 206: p. 177-186.

Gustafsson, et al. The 21-Residue Surfactant Peptide (LysLeu4)4Lys(KL4) is a Transmembrane α-helix with a Mixed Nonpolar/Polar Surface. FEBS Letters 384; 1996, 185-188.

(Continued)

*Primary Examiner* — Lianko G Garyu
(74) *Attorney, Agent, or Firm* — Dinsmore & Shohl LLP

(57) ABSTRACT

The present invention in particular relates to the field of micro- and nanoparticles, more in particular to coated nanoparticles. The coatings of the present invention in particular comprise surfactant protein B (SP-B) and one or more lipids. The invention further relates to such coated particles and compositions comprising them for use as a medicament, in particular for use in the treatment of various disorders. Furthermore, the invention provides the use of the compositions of the current invention for delivering one or more agents, such as small interfacing RNA (siRNA) molecules, to the target tissue or cells.

17 Claims, 5 Drawing Sheets

Specification includes a Sequence Listing.

(56) References Cited

OTHER PUBLICATIONS

Olmeda, et al., Structure-Function Correlations of Pulmonary Surfactant Protein SP-B and the Saposin-Like Family of Proteins. Eur Biophys J., 2013, 42: 209-222.
Olmeda, et al., A Model for the Structure and Mechanism of Action of Pulmonary Surfactant Protein B. FASEB Journal, Oct. 2015;29(10):4236-4247.
Parra, et al. Composition, Structure and Mechanical Properties Define Performance of Pulmonary Surfactant Membranes and Films. Chemistry and Physics of Lipids, 2015. 185: p. 153-175.
Pérez-Gil, J., A. Cruz, and C. Casals, "Solubility of Hydrophobic Surfactant Proteins in Organic-Solvent Water Mixtures—Structural Studies on Sp-B and Sp-C in Aqueous-Organic Solvents and Lipids", Biochimica Et Biophysica Acta, 1993. 1168(3): p. 261-270.
Rouser G., et al., Two Dimensional Thin Layer Chromatographic Separation of Polar Lipids and Determination of Phospholipids by Phosphorus Analysis of Spots, Lipids, 1970, 5:494-496.

* cited by examiner

SEQUENCE LISTING

```
<160> NUMBER OF SEQ ID NOS: 6

<210> SEQ ID NO 1
<211> LENGTH: 19
<212> TYPE: RNA
<213> ORGANISM: Artificial Sequence
<220> FEATURE:
<223> OTHER INFORMATION: siRNA Duplex Against Enhanced Green Fluorescent
      Protein Sense Strand

<400> SEQUENCE: 1

caagcugacc cugaaguuc                                                19


<210> SEQ ID NO 2
<211> LENGTH: 19
<212> TYPE: RNA
<213> ORGANISM: Artificial Sequence
<220> FEATURE:
<223> OTHER INFORMATION: siRNA Duplex Against Enhanced Green Fluorescent
      Protein Antisense Strand

<400> SEQUENCE: 2

gaacuucagg gucagcuug                                                19


<210> SEQ ID NO 3
<211> LENGTH: 19
<212> TYPE: RNA
<213> ORGANISM: Artificial Sequence
<220> FEATURE:
<223> OTHER INFORMATION: Non-Targeting Negative Control Duplex Sense
      Strand

<400> SEQUENCE: 3

ugcgcuacga ucgacgaug                                                19


<210> SEQ ID NO 4
<211> LENGTH: 19
<212> TYPE: RNA
<213> ORGANISM: Artificial Sequence
<220> FEATURE:
<223> OTHER INFORMATION: Non-Targeting Negative Control Duplex Antisense
      Strand

<400> SEQUENCE: 4

caucgucgau cguagcgca                                                19


<210> SEQ ID NO 5
<211> LENGTH: 21
<212> TYPE: RNA
<213> ORGANISM: Artificial Sequence
<220> FEATURE:
<223> OTHER INFORMATION: siRNA Duplex Against Murine Tumor Necrosis
      Factor Sense Strand

<400> SEQUENCE: 5

caaauggccu cccucucauu u                                             21


<210> SEQ ID NO 6
<211> LENGTH: 21
<212> TYPE: RNA
<213> ORGANISM: Artificial Sequence
<220> FEATURE:
<223> OTHER INFORMATION: siRNA Duplex Against Murine Tumor Necrosis
      Factor Antisense Strand
```

-continued

<400> SEQUENCE: 6

```
augagaggga ggccauuugu u                                               21
```

PARTICLES COMPRISING SURFACTANT PROTEIN B AND ONE OR MORE LIPIDS

SEQUENCE LISTING

This application incorporates by reference the material in the ASCII text file "2019-10-23 Substitute Sequence Listing GHE0029PA_ST25.txt" of 1,898 bytes created on Oct. 23, 2019, and filed herewith.

FIELD OF THE INVENTION

The present invention relates to the field of micro- and nanoparticles, more in particular to particles comprising pulmonary surfactant protein B (SP-B) and one or more lipids. The invention further relates to such particles and compositions comprising them for use as a medicament, in particular for use in the treatment of various disorders. Furthermore, the invention provides the use of the compositions of the current invention for delivering one or more agents, such as small interfering RNA (siRNA) molecules, to the target tissue or cells.

BACKGROUND TO THE INVENTION

Because of their small size, nanoparticles are very promising for the intracellular delivery of various types of drugs, e.g. anticancer and immunomodulatory drugs. In addition, nanoparticles are frequently applied to alter the pharmacokinetics and tissue distribution of a drug, with the aim to improve its therapeutic index. Indeed, nanoparticles can be designed to target specific organs, tissues and cells by modifying their physicochemical properties and/or decorating them with antibodies or other ligands. In addition, nanoparticles can be tailored to release their payload with desired kinetics. As such, nanoparticles are frequently investigated for systemic delivery applications, although their benefit for topical administration (e.g. inhalation therapy, mucosal drug delivery, etc.) has also been convincingly demonstrated. Besides nanoparticles, also microparticles can be internalized by phagocytic cells (e.g. macrophages, dendritic cells), allowing intracellular drug delivery to such cell types. Alternatively, microparticles can also refer to microparticulate powders, produced by e.g. spray drying. Although initial studies in the area of intracellular drug delivery have been performed on the delivery of deoxyribonucleic acid (DNA), there is an increasing interest in the use of micro- and nanoparticles for intracellular delivery of other molecules as well to modulate cell activity.

Furthermore, micro- and nanoparticles can encapsulate or be conjugated to imaging probes and contrast agents, offering unique properties for diagnostic applications. Non-invasive imaging by magnetic resonance imaging (MRI), optical imaging, radionuclide-based imaging and such like, renders them useful in probing (cellular) biological processes and image-guided drug delivery, both in vitro and in vivo. Moreover, particle imaging probes can be applied for labeling of transplanted cells for in vivo cell tracking by non-invasive means, which is also critical to monitor therapeutic efficacy of cell-based therapies.

RNA interference (RNAi) represents a powerful gene silencing mechanism wherein short RNA duplexes, termed small interfering RNA (siRNA), function as the effector molecules for sequence-specific mRNA cleavage, thereby inducing gene-silencing on the post-transcriptional level. Since synthetic siRNAs can activate the RNAi pathway in mammalian cells and since they can be designed to target nearly any human gene, RNAi has become an interesting method to suppress gene expression for therapeutic purposes in humans. Different target tissues and modes of administration have already been evaluated for RNAi.

Macromolecules with an intracellular target, such as siRNA, mostly require delivery into the cytoplasm of target cells. Unfortunately, the cell membrane is largely impermeable for this class of therapeutics. As mentioned above, cellular delivery is typically facilitated by formulating these drugs into polymer- or lipid-based micro- and nanoparticles. They can guide macromolecules into cells through endocytosis, but escape from the endosomal lumen into the cytosol remains a major hurdle for intracellular drug delivery. Both the cell membrane and the endosomal membrane form major barriers to efficient delivery of macromolecular and other membrane-impermeable drugs.

Recently, a bio-inspired hybrid nanoparticle with a core-shell nanoarchitecture, consisting of a siRNA-loaded dextran nanogel (siNG) core and a pulmonary surfactant shell was developed (De Backer et al., 2015). In this publication, the outer shell consisted of the natural-derived pulmonary surfactant Curosurf®, which is composed of a complex mixture of lipid and protein components (Parra et al., 2015). This complex composition can contribute to undesired batch-to-batch variability. Moreover, it is conceivable that many of these components are redundant or even unfavorable in the context of cellular delivery, underscoring the need to reduce the complexity of the delivery formulation.

In the present invention, we present specific lipid and protein components that are vital for designing suitable drug delivery platforms. Interestingly, it was demonstrated that the presence of surfactant protein B (SP-B) in the formulation is vital for the improved siRNA delivery.

The pulmonary surfactant shell as demonstrated herein, increased biological efficacy in cell culture, thereby achieving substantial gene silencing of a model target even at low siRNA dose.

SUMMARY OF THE INVENTION

The present invention relates to the use of a composition comprising surfactant protein B (SP-B), or an SP-B related protein or peptide, and one or more lipids. In particular, said lipids contain a high amount of unsaturated or saturated lipids for preparing or coating particles. Said particles having specific lipid and protein components are demonstrated to be very efficient delivery platforms.

The present invention provides a composition comprising a particle, said particle comprising one or more active agents and a lipid composition, said lipid composition consisting of (a) (pulmonary) surfactant protein B (SP-B), or an SP-B related protein or peptide, and (b) one or more lipids. The composition as provided herein is capable of delivering the active agent across biological membranes (such as the cell membrane and/or the endosomal membrane), either in vivo, in vitro or ex vivo and/or modifying cellular function such as e.g. by gene silencing.

In one embodiment, the invention relates to a micro- or nanoparticle, said particle comprising (a) surfactant protein B (SP-B), or an SP-B related protein or peptide, and (b) one or more lipids. More specific, the particle comprises at least one active agent and a proteolipid composition, said proteolipid composition consisting essentially of (a) surfactant protein B (SP-B), or an SP-B related protein or peptide, and (b) one or more lipids. In particular, the particle is a polymeric particle, more in particular a dextran nanogel, more in particular a cationic dextran nanogel. In a specific embodiment, the surfactant-protein B (SP-B), or the SP-B related protein or peptide, and the one or more lipids are part of the outer layer or coating of the particle.

In a further embodiment, the lipids are phospholipids; in particular a combination of one or more zwitterionic phospholipids and one or more anionic phospholipids. Optionally, one of the lipids is cholesterol. Particular useful phospholipids are selected from the list comprising: 1,2-dioleoyl-sn-glycero-3-phosphocholine (DOPC), 1-palmitoyl-2-oleoyl-sn-glycero-3-phosphocholine (POPC), 1-stearoyl-2-oleoyl-sn-glycero-3-phosphocholine (SOPC), 1,2-dioleoyl-sn-glycero-3-phosphoethanolamine (DOPE), 1,2-dipalmitoyl-sn-glycero-3-phosphocholine (DPPC), 1,2-distearoyl-sn-glycero-3-phosphocholine (DSPC), 1,2-dimyristoyl-sn-glycero-3-phosphocholine (DMPC), 1,2-dilauroyl-sn-glycero-3-phosphocholine (DLPC), L-α-phosphatidylcholine ((egg)PC), L-α-phosphoethanolamine ((egg)PE), 1,2-dioleoyl-sn-glycero-3-phosphatidylglycerol (DOPG), L-α-phosphatidylglycerol ((egg)PG), 1,2-dioleoyl-sn-glycero-3-phosphatidic acid (DOPA), L-α-phosphatidic acid ((egg)PA), or combinations thereof such as e.g. a combination of DOPC:(egg)PG (1,2-dioleoyl-sn-glycero-3-phosphocholine; L-α-phosphatidylglycerol), a combination of DOPC:(egg)PA (1,2-dioleoyl-sn-glycero-3-phosphocholine; L-α-phosphatidic acid), a combination of DPPC:(egg)PG or a combination of DPPC:(egg)PA.

In a further embodiment, said SP-B, or said SP-B related protein or peptide, is present at a weight ratio of about 0.1 wt % to about 5.0 wt % with respect to the complete lipid composition of the particle; more specifically between about 0.4 wt % and about 1.6 wt %.

The particles of the invention are particularly useful in a method for the targeted delivery of an agent to a cell, tissue or subject, in particular for the intracellular delivery of an agent. Hence in one embodiment, the particles are loaded with or coupled to an agent selected from the list comprising: a therapeutic agent, a biologically active agent or a diagnostic imaging agent. More particular, the agent is a small molecule or a macromolecule, in particular a nucleic acid, and even more particular siRNA. Optionally, the particle further comprises a targeting ligand, an imaging agent, a fluorescent agent, a PEGylated lipid or a functionalized lipid.

The present invention also relates to a pharmaceutical composition comprising the particles or a composition comprising these particles as provided herein and a pharmaceutically acceptable excipient, carrier and/or diluent.

In a further embodiment, the present invention encompasses the particles or a composition comprising them for use as a medicament, in particular for use in delivering an agent across the cellular membrane in a subject and/or for use in modulating a cellular function thereby ameliorating or treating disease. The invention thus relates to a method for the intracellular delivery of an agent into a subject, said method comprising administering to said subject a composition comprising a particle loaded with or coupled to the agent, wherein said particle comprises a lipid composition consisting of (a) surfactant protein B (SP-B) and (b) one or more lipids; or wherein said particle is characterized by an outer layer or coating consisting of (a) surfactant-protein B (SP-B), or an SP-B related protein or peptide, and (b) one or more lipids. In a particular embodiment, the lipid composition of the particles is less complex and different from the composition of a natural occurring lung surfactant.

The present invention also relates to a method for the preparation of a micro- or nanoparticle, said method comprising the steps of:

providing particles, either or not preloaded with an agent, coating said particles with a lipid composition consisting of surfactant protein B (SP-B) or an SP-B related protein or peptide, and one or more lipids.

BRIEF DESCRIPTION OF THE DRAWINGS

With specific reference to the figures, it is to be noted that the particulars shown are by way of example and for purposes of illustrative discussion of the different embodiments of the present invention. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings make it apparent to those skilled in the art how the several forms of the invention may be embodied in practice.

DETAILED DESCRIPTION OF THE INVENTION

Figure 1:
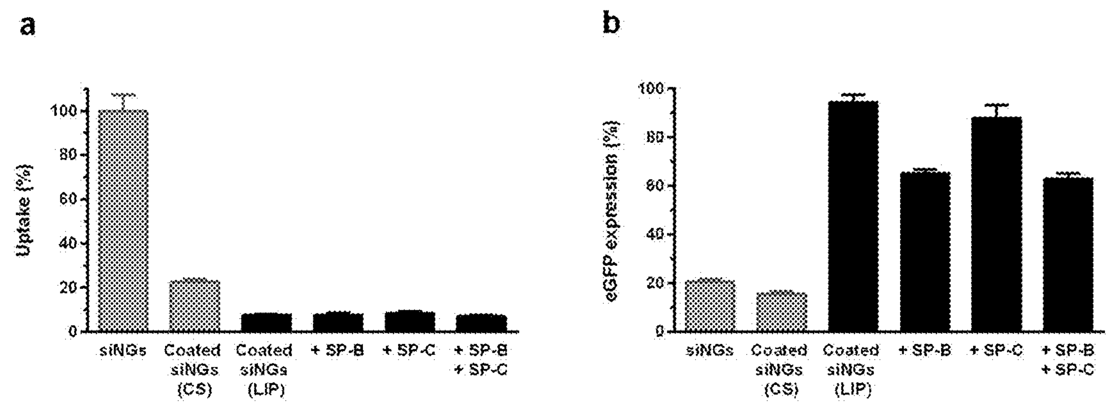
FIG. 1. Biological activity of siNGs coated with surfactant protein containing proteolipid mixtures. Evaluation of (a) cellular uptake and (b) gene silencing potential of siNGs in H1299_eGFP cells determined via flow cytometry. The siNGs were layered with Curosurf® (coated siNGs (CS)) or DPPC:POPC:eggPG (50:35:15 wt %; coated siNGs (LIP)). In this LIP outer layer, SP-B (0.4 wt %) and/or SP-C (0.7 wt %) were incorporated. In the uptake experiments, NGs were loaded with fluorescently labeled control siRNA (siCy5), for which values of the coated formulations are shown relative to the maximal amount of particles taken up, i.e. for uncoated siNGs (100%). The eGFP expression of the cells treated with eGFP-targeting siRNA (siEGFP) was normalized to the expression of cells treated with control siRNA (siCTRL). All experiments were performed with a fixed NG concentration (30 μg/mL) and siRNA concentration (50 nM) (n=3, 1 independent repeat).

The present invention will now be further described. In the following passages, different aspects of the invention are defined in more detail. Each aspect so defined may be combined with any other aspect or aspects unless clearly indicated to the contrary. As used in the specification and the appended claims, the singular forms "a", "an", and "the" include plural referents unless the context clearly dictates otherwise. By way of example, "a compound" means one compound or more than one compound. Throughout the description and claims of this specification the word "comprise" and other forms of the word, such as "comprising" and "comprises," means including but not limited to, and is not intended to exclude, for example, other additives, components, integers, or steps. The terms described above and others used in the specification are well understood to those in the art. All references, and teachings specifically referred to, cited in the present specification are hereby incorporated by reference in their entirety.

The present invention provides compositions that are capable of translocating active agents across a biological membrane. The invention is directed to micro- and nanoparticles and compositions comprising them that can be used to deliver therapeutic, biologically active or diagnostic agents into cells. The particles can be used simultaneously for cell tracking and drug delivery. The particles or compositions can be used as a therapeutic medicine, for the cellular delivery of membrane-impermeable molecules in general, both macromolecular compounds but small molecules as well. Macromolecular compounds may include peptides, proteins, nucleic acids, oligosaccharides, polysaccharides, etc. Application of the particles and compositions can be local (e.g. pulmonary delivery), but also systemic (e.g. intravenous administration). Furthermore, the particles and compositions can be used in the treatment of e.g. inflammatory conditions, neurodegenerative conditions, cancer, cardiovascular pathologies, metabolic pathologies and infectious diseases.

The micro- and nanoparticles of the present invention are characterized by a proteolipid composition comprising, consisting essentially of, or consisting of surfactant-protein B (SP-B) and one or more lipids.

The term "particle" as used herein refers to particles between about 5 nm to about 100 μm in size. The term "microparticle" as used herein means particles between about 1 and about 100 μm in size and includes but is not limited to microspheres, core-shell microparticles, polyelectrolyte microparticles, metallic microparticles, metal-organic framework (MOF) micromaterials, emulsions and microparticulate powders (e.g. obtained via spray drying). The term "nanoparticle" as used herein is taken to mean particles having one or more dimensions at the nanometre scale, i.e. those particles having one or more dimensions between about 5 nm to about 1000 nm, in particular from about 5 nm to about 500 nm, more in particular between 5 nm and 300 nm. Examples of nanoparticles include polymeric nanoparticles, lipid nanoparticles, viral nanoparticles, extracellular vesicles, micelles, metal-organic framework (MOF) nanomaterials, carbon nanomaterials, ceramic nanoparticles, emulsions, metallic particles, quantum dots and others. The particles may be customized in terms of size, surface charge and attachment of any targeting moieties or the like. Any type of micro- and nanoparticles may be used in the present invention; preferably, the nanoparticles are polymeric nanoparticles. The particles of the present invention may be formed from any suitable biocompatible materials, which may be biodegradable or non-biodegradable. Examples of suitable biodegradable materials include collagen, fibrin, chitosan, hyaluronic acid, dextran, poly(anhydrides), poly(hydroxy acids), poly(ortho esters), poly(propylfumerates), poly(caprolactones), polyamides, polyamino acids, polyacetals, biodegradable polycyanoacrylates, biodegradable polyesters, biodegradable polyurethanes, poly (glycerol sebacates), especially elastomeric poly(glycerol sebacates), and polysaccharides. Non-biodegradable, yet biocompatible materials include polypyrrole, polyanilines, polythiophene, polystyrene, polyesters, non-biodegradable polyurethanes, polyureas, poly(ethylene vinyl acetate), polypropylene, polymethacrylate, polyethylene, polycarbonates, and poly(ethylene oxide). Those skilled in the art will recognize that this is not a comprehensive list of materials appropriate for the preparation of micro- and nanoparticles, but rather an illustrative list. In a specific embodiment, the term "particle" does not comprise cationic lipid-based particles such as cationic liposomes. Cationic liposomes can be defined as liposomes that incorporate a substantial fraction of cationic lipids in their lipid composition, in particular at least 5 mol % of cationic lipid, more in particular at least 10 mol % of cationic lipid, even more in particular at least 20 mol %, 30 mol %, 40 mol %, 60 mol % or 80 mol % of cationic lipid.

More specific, the polymeric particles of the invention in particular include a cationic agent embedded in the particle core and/or on the surfaces of the particles. Where the particles are to be complexed with nucleic acids as the therapeutic agent, the positively charged particles are believed to interact electrostatically with the negatively charged DNA/RNA molecules, which not only facilitates complexation of the therapeutic, but which may also protect the latter from enzymatic degradation. Preferably, the cationic agent may be a polycationic agent such as but not limited to chitosan, protamines, peptides (such as poly(L-lysine), poly(L-arginine)), peptide derivatives (such as poly (L-lysine)-palmitic acid), polyethylenimine, poly(amido ethylenimine), and poly(amido amine)s. A preferred polycationic agent is a polymer, preferably a polysaccharide, more preferably dextran, which is functionalized with a reactive (meth)acrylate moiety and subsequently co-polymerized with a cationic (meth)acrylate monomer such as 2-aminoethyl methacrylate, 2-(diethylamino)ethyl methacrylate, 2-(dimethylamino)ethyl methacrylate, 2-N-morpholinoethyl methacrylate, 2-(tert-butylamino)ethyl methacrylate, 2-(diisopropylamino)ethyl methacrylate, or [2-(methacryloyloxy)-ethyl] trimethylammonium chloride.

In a specific embodiment, the nanoparticle is a cationic dextran nanogel, as described and prepared in De Backer et al., 2013 (incorporated herein by reference). Hence, the present invention relates to cationic dextran nanogels having a coating consisting of surfactant protein B and one or more lipids.

"Surfactant protein-B" (SP-B) is an essential lipid-associated protein found in lung surfactant as is described e.g. in Olmeda et al., 2013. The protein can be commercially obtained, produced recombinant, or synthetically, or isolated from lung surfactant, clinical surfactant preparations or animal lungs. The isolation protocol typically contains an organic solvent extraction or detergent solubilisation step, followed by size-exclusion or ion-exchange chromatography, as described e.g. in Olmeda et al., 2015. Commercially available modified surfactant preparations are, for example, poractant alfa (Curosurf®), derived from porcine lung, calfactant (Infasurf®) and bovactant (Alveofact®) extracted from calf/bovine lung lavage, and beractant (Survanta®), a chemically modified natural bovine lung extract. Moreover, SP-B-related peptides or proteins that mimic the cationic and amphiphilic properties of the native SP-B protein, such as SP-B analogs or SP-B mimetics, can also be used. SP-B mimetics include but are not limited to (poly)peptides as described in WO2014/079898 (incorporated herein by reference) and WO2013/120058 (incorporated herein by reference); precursor(s) of the mature SP-B (e.g. pro-SP-B), as it is formed in alveolar type II cells; Mini-B, i.e. a 34-residue peptide with internal disulfide linkages that is composed of the N- and C-terminal helical regions of SP-B; Super Mini-B, with native SP-B residues (residues 1-7) attached to the N-terminus of Mini-B; SP-B(1-25), a synthetic peptide derived from the N-terminal domain of SP-B (containing residues 1-25) and KL4, a synthetic peptide that mimics the cationic and amphiphilic properties of the native SP-B protein. Pro-SP-B can also be produced recombinant. The term "analogs of surfactant protein SP-B", includes (poly) peptides having an amino acid sequence in which, compared to the native protein or to the above described SP-B mimics, possibly one or more amino acids are excluded or have been replaced by other amino acids, but in a lipid mixture such as a phospholipid mixture still show surface-active properties as analyzed with e.g. a bubble surfactometer. More specific, analogs of SP-B have a sequence identity of at least 70%, in particular at least 80%, more in particular at least 90% with the native SP-B. As demonstrated herein, only the presence of SP-B in the lipid coating stimulated cytosolic siRNA delivery, resulting in target (e.g. eGFP) gene suppression. The identification of surfactant protein B as the main driver of drug delivery provides opportunities to use this component in diverse drug delivery systems to boost their delivery performance. It is hence a particular advantage of the present invention that micro- and nanoparticles can be prepared with reduced complexity, reduced batch-to-batch variability and improved control over the specific particle composition compared to the complex composition found in e.g. Curosurf®, thereby resulting in an improved biological performance and biocompatibility when used in therapeutic and/or diagnostic applications.

In a specific embodiment, surfactant protein B is present at a weight ratio of 0.1 wt % to 10 wt %; 0.1 wt % to 5 wt %; 0.1 wt % to 1 wt %; or 0.1 wt % to 0.5 wt %, more particular about 0.2 wt % to about 5 wt %, and even more in particular about 0.4 wt % to about 3 wt %, with respect to the complete lipid composition. In a preferred embodiment, the weight ratio is at least or about 0.2 wt %, 0.3 wt % 0.4 wt %, 0.5 wt %, 0.6 wt %, 0.8 wt %, 1 wt %, 1.2 wt %, 1.4 wt %, 1.6 wt %, 2 wt %, 2.5 wt %, 3 wt %, 3.5 wt %, or 4 wt %, and all values in between.

The one or more "lipids" as referred to herein, comprise any lipid composition other than specified for the commercially available surfactant preparations clinically approved for surfactant replacement therapy in premature infants, e.g. Curosurf® (poractant alpha), Infasurf®, Survanta® or Alveofact®. More specific, the one or more lipids are either saturated or unsaturated lipids, or a combination thereof. Saturated lipids are characterized by having fatty acid acyl chains consisting exclusively of single C—C bonds. Unsaturated lipids are defined as lipids in which at least one fatty acid acyl chain contains at least one double C═C bond (e.g. unsaturated neutral lipids, unsaturated sphingolipids (e.g. unsaturated sphingomyelin), unsaturated glycerolipids (e.g. unsaturated mono-, di- or tri-acyl glycerols) and unsaturated fatty acids. Alternatively, neutral lipids with at least one double C═C bond include cholesterol. Even more specific, the one or more lipids are phospholipids, and in particular "unsaturated phospholipids", being phospholipids in which at least one fatty acid acyl chain contains at least one double C═C bond, including either zwitterionic phospholipids, or anionic phospholipids, and combinations thereof. Specific examples of unsaturated phospholipids include but are not limited to 1-palmitoyl-2-oleoyl-sn-glycero-3-phosphocholine (POPC), 1-stearoyl-2-oleoyl-sn-glycero-3-phosphocholine (SOPC), 1,2-dioleoyl-sn-glycero-3-phosphocholine (DOPC), 1,2-dioleoyl-sn-glycero-3-phosphoethanolamine (DOPE), L-α-phosphatidylcholine ((egg)PC), L-α-phosphatidylethanolamine ((egg)PE) (examples of zwitterionic unsaturated phospholipids) and 1,2-dioleoyl-sn-glycero-3-phosphatidylglycerol (DOPG), L-α-phosphatidylglycerol ((egg)PG), 1,2-dioleoyl-sn-glycero-3-phosphatidic acid (DOPA), L-α-phosphatidic acid ((egg)PA) (examples of anionic unsaturated phospholipids) and combinations thereof. In an alternative embodiment, the lipids of the lipid composition are mainly "saturated phospholipids", being phospholipids with fatty acid acyl chains consisting exclusively of single C—C bonds. Specific examples include 1,2-distearoyl-sn-glycero-3-phosphocholine (DSPC), 1,2-dipalmitoyl-sn-glycero-3-phosphocholine (DPPC), 1,2-dimyristoyl-sn-glycero-3-phosphocholine (DMPC), 1,2-dilauroyl-sn-glycero-3-phosphocholine (DLPC), 1,2-distearoyl-sn-glycero-3-phosphoethanolamine (DSPE), 1,2-dipalmitoyl-sn-glycero-3-phosphoethanolamine (DPPE) (examples of zwitterionic saturated phospholipids) and 1,2-dipalmitoyl-sn-glycero-3-phosphatidylglycerol (DPPG), 1,2-dipalmitoyl-sn-glycero-3-phosphatidic acid (DPPA) (examples of anionic saturated phospholipids). In a specific embodiment, the lipids are phosphatidylcholine (PC) phospholipids. The concentration (weight %) of said saturated or unsaturated (phospho)lipids in the proteolipid composition of the micro- or nanoparticles is in particular at least 60%, in particular at least 65%, even more particular at least 70%, 75%, 80%, 85%, or 90% and even up to near 100%, i.e. 99%, 99.5%, 99.6%, 99.7%, 99.8% or 99.9%. Particular ranges of weight % of (phospho)lipids in the coating of the particles are 70-99.8%, in particular 85-99.8%, more in particular 90-99.8%. It has been demonstrated herein that using SP-B in combination with high amounts of either unsaturated phospholipids or saturated phospholipids in the composition or coating significantly promoted gene silencing. This is in contrast to commercially available surfactant compositions which typically contain lower levels of either saturated or unsaturated phospholipids. Hence, having both surfactant protein B and a high amount of unsaturated or saturated (phospho)lipids in the specific proteolipid composition increases both biocompatibility and biological performance.

In great contrast with Curosurf® which consists of a significant fraction of surfactant protein C and with a relatively limited concentration of saturated or unsaturated phospholipids, the nanoparticles of the present invention, or composition comprising them, contain no surfactant protein C and a substantial higher amount of saturated and/or unsaturated (phospho)lipids. Furthermore, in one embodiment it was found that DOPC, which constitutes only a minor fraction of Curosurf®, proved to be an efficient coating component in combination with SP-B. In another embodiment, it was demonstrated that particles comprising a lipid composition comprising a high amount of DPPC in combination with SP-B resulted in an efficient target gene suppression. Curosurf® contains up to 56 wt % of DPPC and fatty acid patterns within the PC lipid fraction show a 6-7 fold higher amount of palmitic acid compared to oleic acid. (Blanco and Perez-Gil, 2007).

In one embodiment, the phospholipids are selected from 1,2-dipalmitoyl-sn-glycero-3-phosphocholine (DPPC), 1-palmitoyl-2-oleoyl-sn-glycero-3-phosphocholine (POPC), L-α-phosphatidylglycerol (eggPG), 1,2-dioleoyl-sn-glycero-3-phosphocholine (DOPC), L-α-phosphatidic acid (eggPA), and combinations thereof. More specific, the phospholipids are a combination of DOPC:PG (1,2-dioleoyl-sn-glycero-3-phosphocholine; L-α-phosphatidylglycerol), DOPC:PA (1,2-dioleoyl-sn-glycero-3-phosphocholine; L-α-phosphatidic acid), DPPC:PG (1,2-dipalmitoyl-sn-glycero-3-phosphocholine, L-α-phosphatidylglycerol) or DPPC:PA (1,2-dipalmitoyl-sn-glycero-3-phosphocholine, L-α-phosphatidic acid), and more specific a combination of DOPC:eggPG (1,2-dioleoyl-sn-glycero-3-phosphocholine; L-α-phosphatidylglycerol (egg, chicken)) DOPC:eggPA (1,2-dioleoyl-sn-glycero-3-phosphocholine; L-α-phosphatidic acid (egg, chicken)), DPPC:eggPG ((1,2-dipalmitoyl-sn-glycero-3-phosphocholine; L-α-phosphatidylglycerol (egg, chicken)) or DPPC:eggPA ((1,2-dipalmitoyl-sn-glycero-3-phosphocholine; L-α-phosphatidic acid (egg, chicken)).

In particular, said DOPC:(egg)PG or DPPC:(egg)PG has a ratio of about 75:25, 85:15, or 90:10, or said DOPC:(egg)PA or DPPC:(egg)PA has a ratio of about 75:25, 85:15, or 90:10.

In a further embodiment, the particles' proteolipid composition consists of SP-B and a lipid composition including at least 5 mol %, more specific at least 15 mol %, or even more specific at least 30 mol % of cholesterol. For cholesterol concentrations exceeding 30 mol %, the so-called liquid ordered phase is dominant and no main phase transition of the phospholipid(s) with which the cholesterol is mixed can be observed anymore over a broad range of temperatures. It can be an advantage to add such cholesterol amounts to the particle proteolipid composition since it has been demonstrated for lipid nanoparticles that high concentrations of cholesterol (>30 mol %), e.g. in combination with phosphatidylcholine, increases liposomal stability, drug retention and circulation time following intravenous administration. As demonstrated herein, a negative effect of cholesterol on siRNA delivery was not observed. Such a composition is again in great contrast with Curosurf®, in which neutral lipids like cholesterol and cholesterol esters are removed from the final product through liquid-gel chromatography. Such a composition is also in great contrast with other clinical surfactant preparations, as they typically contain a cholesterol fraction ≤5% by weight (Blanco and Perez-Gil, 2007).

The micro- or nanoparticles as described herein are loaded with or coupled to an agent such as a therapeutic agent, a biologically active agent or a diagnostic (imaging) agent.

Hence, the particles are suitable for use with any drug or (therapeutic) agent. The agent may be encapsulated by the particle or it may be attached to a surface or surfaces thereof to form a conjugate. The particles can also contain bioactive lipids or lipophilic/amphiphilic small molecule compounds or drugs. One particular example is the inclusion of amphiphilic TLR agonists such as monophosphoryl lipid A (MPLA) for vaccination strategies.

In some cases, the encapsulation of the therapeutic agent is advantageous, as higher concentrations of a drug can be encapsulated than attached at the surface. Suitable methods for micro- or nanoparticle preparation and encapsulating therapeutic agents inside particles are known to the skilled person and include but are not limited to electrostatic complexation, covalent coupling, hydrophobic interactions, passive loading, remote loading, salting-out, nanoprecipitation, emulsion-diffusion, solvent-evaporation, spray drying and emulsion polymerization, and is demonstrated in the present examples. Typically such methods may be adapted depending upon the materials used to make the particles and the chosen agent, which adaptation will be within the remit of the skilled person.

As used herein, the “therapeutic agent” may be a protein, peptide, lipid, chemical compound, genetic material (i.e. a nucleic acid) or any other active molecule.

Examples of proteinaceous therapeutic agents that may be delivered intracellularly by the micro- or nanoparticles described herein include enzymes, peptides, antibodies and protein modulators.

Alternatively, the therapeutic agent may be a small molecule, such as daunorubicin, doxorubicin, vincristine, paclitaxel, amphotericin B, morphine, dexamethasone, retinoic acid and histamine, among others. Increasing the specificity of intracellular delivery of small molecules would not only reduce side effects but also the necessary amount of drug and, consequently, costs. The micro- and nanoparticles described herein may similarly increase the specificity of intracellular delivery of small molecules. This could be advantageous, particularly for anticancer drugs and such like, where minimizing the potential side effects and overcoming drug resistance is key.

In a particular embodiment, the therapeutic agent may be genetic material (i.e. a nucleic acid), such as plasmid DNA, messenger RNA (mRNA), DNA antisense oligonucleotides, RNA antisense oligonucleotides, triplex forming oligonucleotides, small non-coding RNAs (e.g. siRNA or miRNA) and long non-coding RNAs. Particularly preferred are complexes of nanoparticles and siRNAs. RNA interference (RNAi) represents a powerful gene silencing mechanism wherein ~21 nt RNA duplexes, i.e. siRNAs, function as the effector molecules for sequence-specific mRNA cleavage, thereby inducing sequence-specific gene-silencing on the post-transcriptional level. Since synthetic siRNA have been shown to activate the RNAi pathway and they can be designed to target nearly any human gene, RNAi has become the method of choice to suppress gene expression for therapeutic purposes.

Furthermore, the lipids of the proteolipid composition can be modified (e.g. with polyethylene glycol) or functionalized (e.g. with a reactive group), which can enhance colloidal stability and circulation time or modifies the surface of the particle with targeting moieties, imaging agents, etc.

In a further embodiment, the micro- or nanoparticles include an imaging agent. As used herein, the term “imaging agent” can mean any agent that can be tracked non-invasively using magnetic resonance imaging (MRI), ultrasound, optical imaging (fluorescence, bioluminescence), confocal microscopy or such like. Suitable imaging agents include, for example fluorine compounds, such as perfluorocarbons (PFCs), and fluorescent labels, such as fluorescent dyes, well known to the skilled person. Examples of suitable fluorescent labels include fluorescein (such as fluoresceinamine or fluorescein isothiocyanate (FITC)), rhodamine, Alexa Fluor® dyes, DyLight® Fluor dyes, ATTO dyes, boron-dipyrromethene (BODIPY) dyes and such like.

It can be an advantage that the particles include at least one imaging agent, as this permits the particles to be tracked in cells in vitro and/or in vivo. The imaging agent may be included in the particles by any suitable means including encapsulation, covalent conjugation, physical immobilisation (for example, by electrostatic complexation, hydrophobic interaction and such like), layer-by-layer (LBL) adsorption and so on. The particular method used will depend upon the particular imaging agent and the micro- or nanoparticles selected, and such methodology would be within the remit of a skilled person.

Furthermore, the micro- and nanoparticles described herein may comprise a ligand or a cell trafficking agent, such as a nuclear localization signal, a mitochondrial localization signal, an ER signal peptide, an ER retrieval sequence or such like, as is described in the art.

The micro- and nanoparticles of the present invention are particularly useful for medical applications such as therapeutic, diagnostic or theranostic applications. The composition of the present invention facilitates the passage, or translocation, of an agent across a biological membrane, particularly into the cytoplasm or nucleus, of the cell. Intracellular events can be more effectively affected and regulated upon intracellular delivery of different biologically active agents using said compositions. These active agents may modify or normalize the cellular function or may eliminate unwanted cells when needed. The changing of the cellular functionality can include a change in a physico-chemical property of the cell, a change in proliferative property of the cell, a change in surviving ability of the cell, a change in secretory capacity of the cell, a change in migration property of the cell and/or a change in morphological phenotypical property of the cell. Hence, many clinical applications can be envisaged. For example, the loaded particles or cells labeled with the particles of the invention could be administered to patients suffering from a disease or disorder whereby the development of the symptoms or conditions associated with said disease are prevented, delayed, alleviated, arrested or inhibited.

In a particular embodiment, the particles are useful for nucleic acid therapy and/or for the prophylaxis and/or treatment of allergy- and immune-related diseases, dermatologic diseases, cardiac diseases, endocrine diseases, metabolic diseases, hematologic diseases, gastrointestinal diseases, colorectal diseases, infectious diseases, cancer, kidney diseases, pulmonary related diseases, rheumatologic diseases, neurological diseases, osteopathic diseases, orthopedic diseases, ophthalmological diseases, otolaryngology related diseases, urological diseases.

The invention thus provides pharmaceutical compositions and delivery systems comprising a micro- or nanoparticle as described herein and a pharmaceutically acceptable excipient, carrier and/or diluent. The invention provides first and further medical uses of the micro- or nanoparticles, compositions and transfected cells. More particular, the present invention provides micro- and nanoparticles for use in the intracellular delivery of an agent, especially a membrane-impermeable agent or a hydrophobic agent or drug, in particular a nucleic acid. The nucleic acid may be administered to suitable cells, ex vivo or in vitro, and the nucleic acid-containing cells may then be transplanted into the patient. Alternatively, the nucleic acid is administered to target organs, tissues and cells in vivo.

The particles or compositions comprising them may be used in a medicament which may be used in a monotherapy (i.e. use of the active agent) for treating, ameliorating or preventing a disease. Alternatively, the particles or compositions comprising them may be used as an adjunct to, or in combination with, known therapies which may be used for treating, ameliorating or preventing a disease. For example, in certain embodiments the treatment of cancer involves administering particles of the invention alone. In certain embodiments the treatment further includes administering to the subject an anti-cancer medicament or treatment e.g. chemotherapeutic agents or radiation. There may be synergistic therapeutic benefits for the co-use of particles as described herein and a known medicament. Compositions comprising the micro- or nanoparticles may be administered in a number of ways, e.g. by oral administration, by inhalation, by intranasal administration, by injection (into the blood stream or directly into a site requiring treatment), as topical use, or incorporated within a slow- or delayed-release device. In a specific embodiment, compositions comprising the particles are administered by inhalation for treatment of pulmonary related diseases. Of note and in contrast with cationic dextran nanogels, it has been described in the literature (De Backer et al., 2013) that cationic liposomes, complexing siRNA, are not compatible with pulmonary surfactant, likely due to lipid mixing leading to (premature) release of the complexed siRNA. In a preferred embodiment, the particles of the invention are administered by inhalation.

Furthermore, the composition may be injected intramuscularly, intravenous (bolus or infusion), intra-arterial (bolus or infusion), subcutaneous (bolus or infusion), or intradermal (bolus or infusion). The frequency of administration will also be influenced by the half-life of the active agents within the subject being treated. Optimal dosages to be administered may be determined by those skilled in the art, and will vary with the particular micro- or nanoparticles or cells in use, the mode of administration, and the advancement of the disease. Additional factors depending on the particular subject being treated will result in a need to adjust dosages, including subject age, weight, gender, diet and time of administration.

The particles may be administered before, during or after onset of the disease, disorder or condition to be treated. Daily doses may be given as a single administration (e.g. a single daily injection). Alternatively, the particles may require administration twice or more times during a day.

The nanoparticles used in the described therapeutic applications may be any of those described herein. Preferably, the nanoparticles comprise a core of cationic dextran nanogel coated with SP-B and one or more lipids, in particular at least 70% saturated or unsaturated phospholipids. Specifically, the therapeutic agent is an siRNA.

A "subject", as used herein, may be a vertebrate, mammal or domestic animal. Hence, compositions or medicaments according to the invention may be used to treat any mammal, for example livestock (e.g. a horse), pets, or may be used in other veterinary applications. Most preferably, the subject is a human being.

A "pharmaceutically acceptable excipient" as referred to herein, is any known compound or combination of known compounds that are known to those skilled in the art to be useful in formulating pharmaceutical compositions. In one embodiment, the pharmaceutically acceptable excipient may be a solid, and the composition may be in the form of a powder or tablet. A solid pharmaceutically acceptable excipient may include one or more substances which may also act as flavouring agents, lubricants, solubilisers, suspending agents, dyes, fillers, glidants, compression aids, inert binders, sweeteners, preservatives, coatings, or tablet-disintegrating agents. The excipient may also be an encapsulating material. In powders, the excipient is a finely divided solid that is in admixture with the finely divided active agents according to the invention. Suitable solid excipients include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like. In addition, the pharmaceutical excipient may be a liquid, and the pharmaceutical composition may be in the form of a solution. Liquid excipients are used in preparing solutions, suspensions, emulsions, syrups, elixirs and pressurised compositions. The particle or agent according to the invention may be dissolved or suspended in a pharmaceutically acceptable liquid excipient such as water, an organic solvent, a mixture of both or pharmaceutically acceptable oils or fats. The liquid excipient can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid excipients for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the excipient can also be an oily ester such as ethyl oleate and isopropyl myristate. Sterile liquid excipients are useful in sterile liquid form compositions for parenteral administration.

Liquid pharmaceutical compositions, which are sterile solutions or suspensions, can be utilised by, for example, subcutaneous, intrathecal, epidural, intraperitoneal, intravenous and particularly intramuscular injection.

The invention also provides in a further aspect, a process for making the (pharmaceutical) composition, the process comprising combining an active agent with the micro- or nanoparticles and a pharmaceutically acceptable excipient. More specific, a specific method for preparing a particle as described herein comprises the steps of:

providing particles, either or not preloaded with an agent;

layering or coating said particles with a coating composition consisting of surfactant protein B and one or more lipids, in particular phospholipids, more in particular at least 70% unsaturated or saturated phospholipids.

In an alternative embodiment, the method for preparing the particle comprises the steps of:

directly preparing particles, either or not preloaded with an agent comprising a proteolipid composition consisting of surfactant protein B and one or more lipids, in particular phospholipids, more in particular at least 70% unsaturated or saturated phospholipids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

EXAMPLES

Materials and Methods

Small Interfering RNAs

For in vitro experiments, 21 nucleotide (nt) small interfering RNA (siRNA) duplexes targeted against Enhanced Green Fluorescent Protein (eGFP), hereafter abbreviated as siEGFP and non-targeting negative control duplexes (siCTRL), were purchased from Eurogentec (Seraing, Belgium). For siEGFP: sense strand=5'-CAAGCUGACCCUGAAGUUCtt-3' (SEQ ID NO:1); antisense strand=5'-GAACUUCAGGGUCAGCUUGtt-3' (SEQ ID NO:2). For siCTRL: sense strand=5'-UGCGCUACGAUCGACGAUGtt-3' (SEQ ID NO:3); antisense strand=5'-CAUCGUCGAUCGUAGCGCAtt-3' (SEQ ID NO:4) (capital letters represent ribonucleotides; lower case letters represent 2'-deoxyribonucleotides). For fluorescence experiments, the siCTRL duplex was labeled with a Cy®5 dye at the 5' end of the sense strand (siCy5). The fluorescent modifications were performed and verified by Eurogentec. The concentration of the siRNA stock solutions in nuclease-free water (Ambion®-Life Technologies, Ghent, Belgium) was calculated from absorption measurements at 260 nm (1 $OD_{260}$=40 μg/mL) with a Nanodrop 2000 spectrophotometer (Thermo Fisher Scientific, DE, USA). For in vivo experiments, stabilized 21 nt siRNA duplexes (siSTABLE), targeted against murine tumor necrosis factor (TNF) α, hereafter abbreviated as siTNFα, and non-targeting negative control duplexes (siCTRL) were purchased from GE Healthcare Dharmacon (Diegem, Belgium). siTNFα sense strand=5'-CAAAUGGCCUCCCUCUCAUUU-3' (SEQ ID NO:5); antisense strand=5'-AUGAGAGGGAGGCCAUUUGUU-3' (SEQ ID NO:6). The sequence of stabilized siCTRL was confidential and could not be listed.

Synthesis of Dextran Nanogels and Loading with siRNA

Cationic dextran nanogels were prepared using an inverse miniemulsion photopolymerization method as reported previously. Briefly, 150 mg of dextran hydroxyethyl methacrylate (dex-HEMA) with a degree of substitution of 5.2 was dissolved in a solution containing 97.5 μL Irgacure 2959 (10 mg/mL in water; Sigma-Aldrich, Bornem, Belgium), 180 μL nuclease-free water and 195 μL of a cationic methacrylate monomer, [2-(methacryloyloxy)-ethyl] trimethylammonium chloride (TMAEMA, 80 wt % solution in water; Sigma-Aldrich). The obtained dex-HEMA solution was emulsified in 5 mL of mineral oil (Sigma Aldrich), supplemented with the surfactant ABIL EM 90 (0.5 mL) (Evonik Goldschmidt GmbH, Essen, Germany), through ultrasonication (90 s, amplitude 15%; Branson Digital Sonifier®, Danbury, USA). The formed emulsified nanodroplets were immediately cross-linked by UV irradiation (900 s, Bluepoint 2.1 UV source, Hönle UV technology, Grafelfing, Germany) under cooling (4° C.). The resulting dex-HEMA-co-TMAEMA nanogels, hereafter abbreviated as NGs, were collected by precipitation in acetone and washed 4 times with acetone:hexane (1:1). Traces of organic solvent were removed by vacuum evaporation and the pellet was redispersed in 5 mL nuclease-free water. To assure long-term stability, the NGs were lyophilized and stored desiccated. To obtain siRNA-loaded NGs (siNGs) for in vitro experiments, a NG stock (2 mg/mL) was prepared by dispersing a weighed amount of lyophilized particles in ice-cooled nuclease-free water, followed by brief sonication (3×5 s, amplitude 10%; Branson Digital Sonifier®, Danbury, USA). Subsequently, equal volumes of NG and siRNA dilutions in 4-(2-hydroxyethyl)-1-piperazineethanesulfonic acid (HEPES) buffer (pH 7.4, 20 mM) were mixed and incubated at 4° C. for ≥15 min to allow complexation. For in vivo experiments, a NG stock (10 mg/mL) was prepared as described above. The NG stock contained less than 0.5 EU/mL lipopolysaccharide (LPS) as determined by the Endosafe®-PTS™ assay (Charles River International, Lecco, Italy). NGs and siRNAs were diluted in nuclease-free water prior to mixing and incubation. In addition, all preparative steps for the in vivo experiments were performed with LPS-free materials under LPS-free conditions. The concentration of siRNA dilutions was adjusted according to the intended dose.

Isolation, Analysis and Quantification of Hydrophobic Surfactant Proteins

The isolation of SP-B and SP-C from native porcine pulmonary surfactant or Curosurf® (a commercially available porcine pulmonary surfactant preparation; Chiesi Farmaceutici, Parma, Italy) was performed as described earlier by Pérez-Gil et al. 1993. For extraction from native porcine lungs, the lungs were first minced and carefully washed. Next, the mixture was filtered and centrifuged (1000 g at 4° C. for 15 min). The supernatant was again centrifuged (3000 g at 4° C. for 2 h) and from the isolated pellet, enriched in large lipid/protein PS complexes, the hydrophobic components including lipids and hydrophobic surfactant proteins were extracted with chloroform/methanol mixtures according to the Bligh & Dyer method. Chromatographic separation in Sephadex LH-20 (GE Healthcare, Machelen, Belgium) of the organic extract allowed separating the hydrophobic protein fraction from the surfactant lipid fractions. A subsequent chromatographic step in Sephadex LH-60 yielded purification of SP-B and SP-C, which were stored in chloroform/methanol solutions. Phospholipid contamination of the protein samples was quantified by phosphorus determination (Rouser et al. 1970). Purity and nature of isolated pools of proteins were analyzed by sodium dodecyl sulfate (SDS) electrophoresis in polyacrylamide gels and subsequent western blot with anti-SP-B and anti-SP-C primary antibodies (Seven Hills, Cincinnati, Ohio, USA). The quantification of the amount of isolated SP-B and SP-C was performed by an amino acid analysis.

Preparation of Curosurf® Coated siRNA-Loaded Nanogels

Prior to the formation of the Curosurf® pulmonary surfactant coat, the NGs were loaded with siRNA, as described above. The unprocessed Curosurf® dispersion (80 mg/mL) was diluted to 4.5 mg/mL in HEPES buffer and incubated with siNGs in equal volumes for 10 min at 4° C., using a Curosurf® to NGs weight ratio of 15 mg/mg. Subsequently, the surfactant coat on the siNGs was formed by sonication (3×10 s, amplitude 10%; Branson Digital Sonifier®, Danbury, USA). This resulted in a hybrid nanoparticle, further denoted as Curosurf® coated siNGs.

Preparation of Proteolipid Coated siRNA-Loaded Nanogels

The following phospholipids were used for siNG coating: 1,2-dipalmitoyl-sn-glycero-3-phosphocholine (DPPC), 1-palmitoyl-2-oleoyl-sn-glycero-3-phosphocholine (POPC), L-α-phosphatidylglycerol (eggPG), and 1,2-dioleoyl-sn-glycero-3-phosphocholine (DOPC). All phospholipids were purchased from Avanti Polar Lipids, Inc. (Alabama, USA). The phospholipids were mixed in chloroform at different weight ratios depending on the experimental needs. In order to incorporate SP-B and/or SP-C in the phospholipid outer layer, the isolated hydrophobic proteins were combined with the phospholipids in chloroform at indicated concentrations. A (proteo)lipid film was formed by rotary evaporation of the organic solvent under vacuum at 37° C. The dried (proteo) lipid film was rehydrated in HEPES buffer by mechanical agitation, resulting in a final (proteo)lipid concentration of 4.5 mg/mL. The hydrated (proteo)lipid film was used in the coating procedure, as described above, for which the ratio of the (proteo)lipid mixture to NGs was 15 mg/mg (in vitro experiments) or 10 mg/mg (in vivo experiments). The (proteo)lipid-siNG mixtures for in vivo administration were diluted 2-fold in nuclease-free water prior to sonication. This resulted in a hybrid nanoparticle further denoted as proteolipid coated siNGs.

Cell Lines and Culture Conditions

Cell culture experiments were performed using human lung epithelial cells (H1299), that stably express the eGFP (H1299_eGFP). H1299_eGFP cells were cultured in RPMI 1640 and DMEM, respectively, supplemented with 2 mM glutamine, 10% fetal bovine serum and 100 U $mL^{-1}$ penicillin/streptomycin at 37° C. in a humidified atmosphere containing 5% $CO_2$. Cells were passed every 3 days using 0.25% trypsin-ethylenediaminetetraacetic acid (EDTA) solution in order to maintain sub-confluency. H1299_eGFP cells were treated with medium containing 1 mg $mL^{-1}$ Geneticin® once per month for selection. All materials were purchased from Gibco®-Life Technologies, except for the serum, which was delivered by Hyclone™ (GE Healthcare, Machelen, Belgium).

Quantification of In Vitro Cellular siRNA Internalization in H1299_eGFP Cells by Flow Cytometry To quantify the cellular uptake of siRNA by flow cytometry, H1299_eGFP cells were seeded in 24-well plates (Greiner Bio-One GmbH, Kremsmünster, Austria) at a density of $2×10^4$ cells/$cm^2$ and left to settle overnight. NGs were loaded with different amounts of siCTRL:siCy5 (100:0.75 mol %) and coated with Curosurf® or a proteolipid mixture using the coating procedure described above. After 5-fold dilution in Opti-MEM® (final NG concentration of 30 μg/mL), the particles were incubated with the cells for 4 h (37° C., 5% $CO_2$). Following incubation, the cells were washed with dextran sulfate sodium salt (0.1 mg/mL in PBS) to remove cell surface-bound fluorescence. Next, the cells were harvested by trypsinization (trypsin/EDTA 0.25%), resuspended in 250 μL, flow buffer (PBS supplemented with 1% bovine serum albumin and 0.1% sodium azide) and incubated on ice until flow cytometry analysis. Transfections were performed in technical triplicate (n=3) per independent repeat and a minimum of $10^4$ cells was analyzed in each measurement, using a FACSCalibur™ flow cytometer (BD Biosciences, Erembodegem, Belgium). Data analysis was performed using the FlowJo™ analysis software (Treestar, Costa Mesa, USA).

Quantification of In Vitro eGFP Silencing in a Lung Epithelial Cell Line by Flow Cytometry H1299_eGFP cells were seeded in 24-well plates (Greiner Bio-One GmbH; $1.85×10^4$ cells/$cm^2$). NGs were loaded with variable amounts of siCTRL or siEGFP. Next, the siNGs were coated with Curosurf® or a proteolipid mixture using the coating procedure described above. After 5-fold dilution in Opti-MEM® (final NG concentration of 30 μg/mL), the particles were incubated with the cells for 4 h (37° C., 5% $CO_2$). Following incubation, non-internalized nanoparticles were washed away with PBS and the cells were incubated with 1 mL fresh cell culture medium for 48 h. The cells were then prepared for analysis by flow cytometry as described above. Transfections were performed in technical triplicate (n=3) per independent repeat and a minimum of $2×10^4$ cells was analyzed in each measurement as described above.

Preparation of Cationic Liposomes with SP-B and Complexation of siRNA

Cationic liposomes were prepared via the lipid film hydration method. All lipids were obtained from Avanti Polar Lipids (USA) as a solution in chloroform. We prepared DOTAP:DOPE liposomes (LPS) mixing appropriate volumes of the lipid solutions in a round bottom flask to obtain a 1:1 molar ratio. Liposomes containing SP-B were prepared by adding an appropriate volume of SP-B solution in chloroform to the mixture of DOTAP and DOPE to obtain a final SP-B concentration of 0.4 wt %. Through rotary evaporation under vacuum at 40° C., a lipid film was created and subsequently hydrated using 1 mL HEPES Buffer (pH 7.4, 20 mM). The obtained mixture was vortexed and sonicated 1 minute at 10% amplitude to obtain a monodisperse LPS dispersion. The LPS were complexed with siRNA immediately before the transfection. Hereto, appropriate dilutions of the LPS in HEPES buffer were incubated with appropriate dilutions of siRNA. The mixture was allowed to complex at 4° C. for 30 minutes prior to further dilution in Opti-MEM and transfection. LPS were complexed with siRNA at a charge ratio equal to 8 and the applied final siRNA concentrations per well were 0.5, 1 and 5 nM.

Ex Vivo Quantification of siRNA Uptake by Different Immune Cell Types and Assessment of Acute In Vivo Toxicity and Cellular Influx in Naive BALB/c Mice Female BALB/c mice were purchased from Charles River Italy and housed under specific pathogen-free conditions in individually ventilated cages in a controlled 12 h day-night cycle and given food and water ad libitum. All mice were 8 weeks old at the start of the experiments. All procedures involving animals were approved by the local Ghent University ethics committee (accreditation nr. LA1400536, Belgium), in accordance with European guidelines. The (proteolipid coated) siNGs and control suspensions for administration were prepared as described above, followed by a 2-fold dilution in 2 times concentrated PBS. Per mice, a dose of 100 μg NG loaded with 1 pmol siTNFα per μg NG was administered. Mouse tracheal aspiration was used for NP administration. Briefly, after sedation with isoflurane (inhalation at 4% for induction and 3% for maintenance), individual mice were placed in a near-vertical position. The animal's tongue was extended with lined forceps, and 80 μL of the NP suspension was instilled posterior of the pharynx. The tongue was held in position until the dispersion was inhaled into the lungs. Control mice were administered 80 μL, of PBS. 24 h after NP administration, mice received a lipopolysaccharide (LPS) dose of 5 μg in 80 μL, PBS via tracheal aspiration. 48 h after NP administration, thus 24 h after LPS administration, the mice were sacrificed by intraperitoneal injection of a lethal dose of Nembutal® (pentobarbital, 200 mg/kg in PBS; Ceva, Brussels, Belgium). Immediately after death, a lavage cannula was placed into the trachea through a small incision. The lungs were flushed once with 1 mL $Ca^{2+}$— and $Mg^{2+}$— free Hank's balanced salt solution (HBSS; Invitrogen™-Life Technologies), supplemented with 0.05 mM EDTA (Sigma-Aldrich). The obtained BAL was subsequently centrifuged (400 g, 7 min, 4° C.), to separate the cellular fraction from the supernatant. The BAL supernatant was quantified for mouse TNFα with a Bio-Plex® Suspension array system (Biorad, Hercules, USA) as described above.

Statistical Analysis

All data are presented as mean±standard deviation (SD). Statistical analysis was performed via One-way ANOVA followed by a Tukey's multiple comparison test, using GraphPad Prism software version 6. Error bars for all experiments represent SD. Error bars for in vivo silencing represent standard error of mean (SEM).

Results

Evaluation of Surfactant Proteins

In order to identify the components of the pulmonary surfactant layer that are responsible for the enhanced siRNA delivery efficiency the surfactant proteins (SP) SP-B and SP-C were isolated from both native porcine lung extracts and Curosurf® (Pérez-Gil et al., 1993).

To discriminate the importance of both surfactant proteins, a lipid mixture composed of 1,2-dipalmitoyl-sn-glycero-3-phosphocholine:1-palmitoyl-2-oleoyl-sn-glycero-3-phosphocholine:L-α-phosphatidylglycerol (DPPC:POPC:eggPG; 50:35:15 wt %) was supplemented with isolated SP-B and/or SP-C, using comparable weight ratio's as documented for Curosurf® (i.e. 0.4 wt % SP-B and 0.7 wt % SP-C (Parra et al., 2015).

As depicted in FIG. 1*a*, the presence of a lipid or lipid-protein outer layer, independent of the composition, markedly reduced the uptake of siNGs in H1299_eGFP. Importantly, if the outer layer consists solely of a model phospholipid mixture (coated siNGs (LIP)), the gene silencing potential of the siNGs was completely inhibited (FIG. 1*b*). This is in stark contrast with the Curosurf® coated siNGs (coated siNGs (CS)).

Interestingly, isolated surfactant-associated proteins can significantly affect the level of gene knockdown obtained with the hybrid formulation (FIG. 1*b*). Despite similar poor intracellular siRNA uptake levels compared to coated siNGs (LIP), significant differences in the downregulation of eGFP upon incorporation of SP-B or SP-C in the lipid coat were observed. Apparently, only the presence of SP-B in the outer layer significantly stimulated cytosolic siRNA delivery, resulting in 40% eGFP gene suppression. The presence of SP-C on the other hand did not significantly alter the gene silencing potential of the coated siNGs (LIP). As a result, the following experiments focused on the use of isolated SP-B in the lipid outer layer.

Evaluation of Saturated vs Unsaturated Phospholipids

Figure 2:
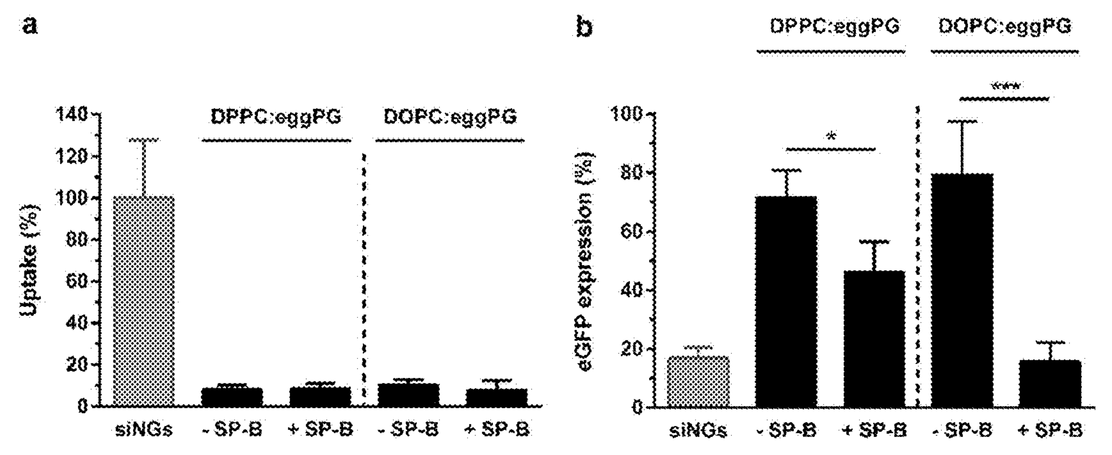
FIG. 2. Impact of the main phospholipid in the outer proteolipid layer on siNGs biological activity. Evaluation of (a) cellular uptake and (b) gene silencing potential of siNGs in H1299_eGFP cells determined via flow cytometry. The siNGs were layered with DPPC:eggPG (85:15 wt %) or DOPC:eggPG (85:15 wt %) in the absence or presence of SP-B (0.8 wt %). In the uptake experiments, NGs were loaded with fluorescently labeled control siRNA (siCy5), for which values of the coated formulations are shown relative to the maximal amount of particles taken up, i.e. for uncoated siNGs (100%). The eGFP expression was normalized to the expression of cells treated with control siRNA (siCTRL). All experiments were performed with a fixed NG concentration (30 μg/mL) and siRNA concentration (50 nM) (n=3, 2 independent repeats; $*p\leq0.05$, $***p\leq0.001$).

First, we evaluated if similar biological effects can be achieved if the lipid mixture used for siNG coating, is reduced to a binary phospholipid mixture. In addition, we opted to compare the efficacy of siNGs layered with DPPC:eggPG (85:15 wt %) with that of siNGs layered with DOPC:eggPG (85:15 wt %), to assess the impact of membrane fluidity. Both are a combination of the negatively charged eggPG (required for interaction with and coating of the cationic siNGs) with a phosphatidylcholine (PC) phospholipid. The only difference is that the DPPC includes solely saturated fatty acid chains, while in DOPC only unsaturated fatty acids are present. The results show that, independent of the applied phospholipid mixture and independent of the presence of SP-B, the cellular internalization of siNGs was markedly inhibited after coating (FIG. 2*a*). The latter resulted in negligible gene knockdown in the absence of SP-B. Coating the siNGs with the SP-B supplemented DPPC:eggPG mixture generated a similar level of knockdown compared with the previous results on DPPC:POPC:eggPG (LIP). Use of a proteolipid composition comprising DOPC significantly promoted gene silencing, reaching comparable levels of knockdown as measured for uncoated siNGs or Curosurf®-coated siNGs (FIG. 2*b*).

Evaluation of Anionic Phospholipids

Figure 3:
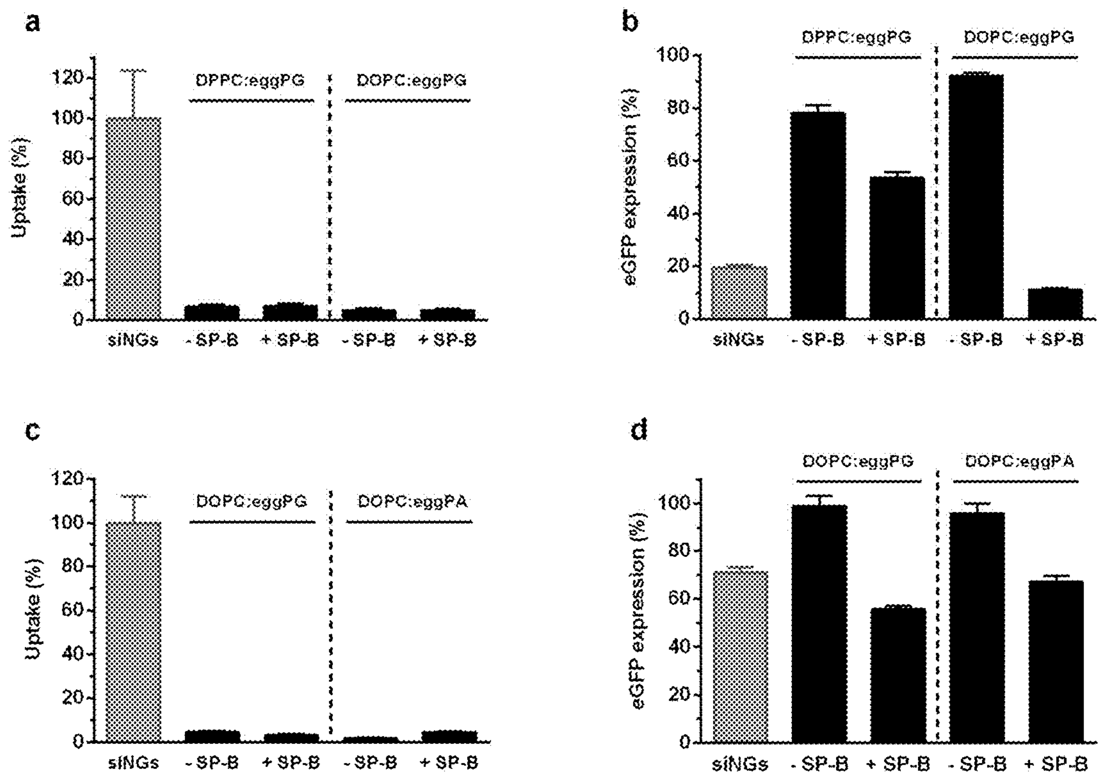
FIG. 3. Evaluation of cellular uptake (a,c) and gene silencing potential (b,d) of siNGs in H1299_eGFP cells, determined via flow cytometry. (a,b) The siNGs were layered with DPPC:eggPG (85:15 wt %) or DOPC:eggPG (85:15 wt %) in the absence or presence of SP-B (0.4 wt %). These experiments were performed with 50 nM siRNA (15 pmol siRNA per well). (c, d) The siNGs were layered with DOPC:eggPG (85:15 wt %) or DOPC:eggPA (85:15 wt %). These experiment were performed with 10 nM siRNA (3 pmol siRNA per well). (n=3, technical replicates). In the uptake experiments, NGs were loaded with fluorescently labeled siRNA (siCy5). The eGFP expression was normalized to the expression of cells treated with control siRNA. All experiments were performed with a fixed NG concentration (30 μg $mL^{-1}$).

Replacing the eggPG by another anionic phospholipid, namely L-α-phosphatidic acid (eggPA), did not have an impact on the cellular internalization and only a minor negative effect on the gene silencing potential (FIG. 3). Of note, given the maximal gene silencing obtained for the DOPC:eggPG:SP-B formulation (FIG. 2*b*), in this experiment we have utilized a suboptimal amount of siRNA (five-fold reduction in siRNA dose), allowing to more precisely monitor marginal effects. This explains why the maximal gene silencing observed for siNGs coated with DOPC:eggPG in the presence of SP-B, was reduced to 60% in FIG. 3*d* compared to 90% reduction in FIG. 3*b*.

Evaluation of Surfactant Proteins with Unsaturated Phospholipid Coat

Figure 4:
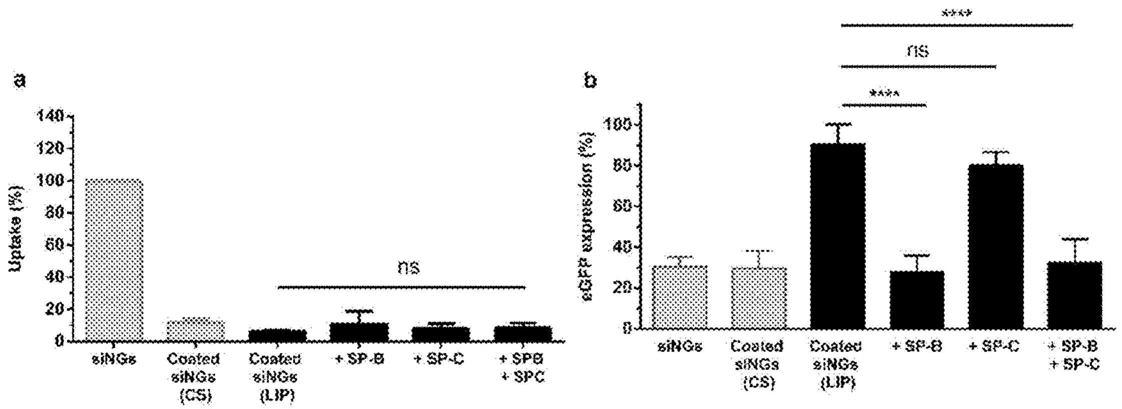
FIG. 4. Biological activity of siNGs coated with a DOPC:eggPG mixture supplemented with different surfactant protein combinations. Evaluation of (a) cellular uptake and (b) gene silencing potential of siNGs in H1299_eGFP cells determined via flow cytometry. The siNGs were layered with Curosurf® (coated siNGs (CS)) or DOPC:eggPG (85:15 wt %; coated siNGs (LIP)). In this LIP outer layer, SP-B (0.4 wt %) and/or SP-C (0.7 wt %) were incorporated. In the uptake experiments, NGs were loaded with fluorescently labeled siRNA (siCy5), for which values of the coated formulations are shown relative to the maximal amount of particles taken up, i.e. for uncoated siNGs (100%). The eGFP expression was normalized to the expression of cells treated with control siRNA (siCTRL). All experiments were performed with a fixed NG concentration (30 μg/mL) and siRNA concentration (50 nM) (n=3, 3 independent repeats). Silencing experiments with SP-C alone are based on 2 independent repeats (****$p \leq 0.0001$).

Having established the importance of unsaturated phospholipids to accommodate the SP-B and to achieve optimal knockdown levels, we next sought to confirm the essential role of the SP-B as compared to SP-C when used in such a phospholipid composition. To this end, we layered siNGs with a DOPC:eggPG (85:15 wt %) lipid coat, supplemented with SP-B (0.4 wt %), SP-C (0.7 wt %) or a combination of both surfactant proteins. As clearly demonstrated in FIG. 4, only if the SP-B is present in the proteolipid coat, a substantial gene knockdown can be noted, confirming the absolute necessity to include SP-B in the formulation as well as the absence of a delivery promoting effect for the SP-C when combined with unsaturated phospholipids.

Evaluation of Cholesterol

Figure 5:
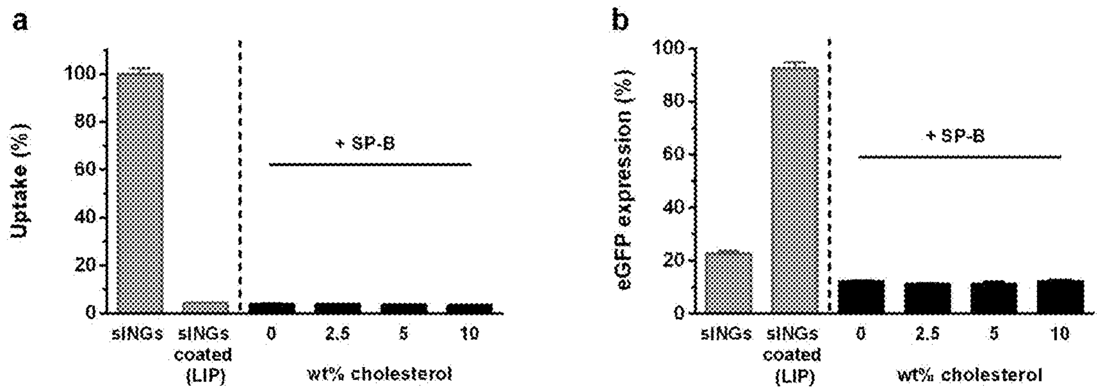
FIG. 5. Impact of cholesterol in the outer layer. Evaluation of (a) cellular uptake and (b) gene silencing potential of siNGs in H1299_eGFP cells, determined via flow cytometry. The siNGs were layered with DOPC:eggPG (85:15 wt %; coated siNGs (LIP)). Isolated SP-B (0.8 wt %) and an increasing amount of cholesterol, varying from 2.5, 5, to 10 wt %, were incorporated in the lipid outer layer. In the uptake experiments, NGs were loaded with fluorescent siRNA (siCy5). The eGFP expression was normalized to the expression of cells treated with control siRNA. All experiments were performed with a fixed NG concentration (30 μg $mL^{-1}$) and siRNA concentration (100 nM). (n=3, technical replicates).

In the native pulmonary surfactant, cholesterol fulfills an important role as it intercalates between the phospholipids enhancing their molecular mobility. The impact of cholesterol, being removed during the preparation of the clinically approved Curosurf® and being absent in the previously evaluated synthetic outer layer compositions, has not yet been explored. The cholesterol content in native pulmonary surfactant equals ±3-8 wt % (Parra et al., 2015). Therefore, we have incorporated 2.5, 5, or 10 wt % cholesterol in the outer layer consisting of DOPC:eggPG (85:15 wt %) and 0.4 wt % SP-B. No significant negative effects on both siNG uptake and protein knockdown levels were observed (FIG. 5).

Evaluation of Source of Surfactant Protein

We have directly compared the cellular effects of different isolated SP-B fractions. One fraction has been isolated from Curosurf®, while three other SP-B fractions were isolated from three different native porcine surfactant samples. The different SP-B fractions have been added to the synthetic binary phospholipid mixture DOPC:eggPG, resulting in a 0.4 wt % SP-B. It can be clearly derived from FIG. 6*a* and FIG. 6*b*, that the observed effects on cellular uptake and model target gene silencing were not or only limited affected by the source from where SP-B is isolated.

Evaluation of Concentration of Surfactant Protein B

Figure 6:
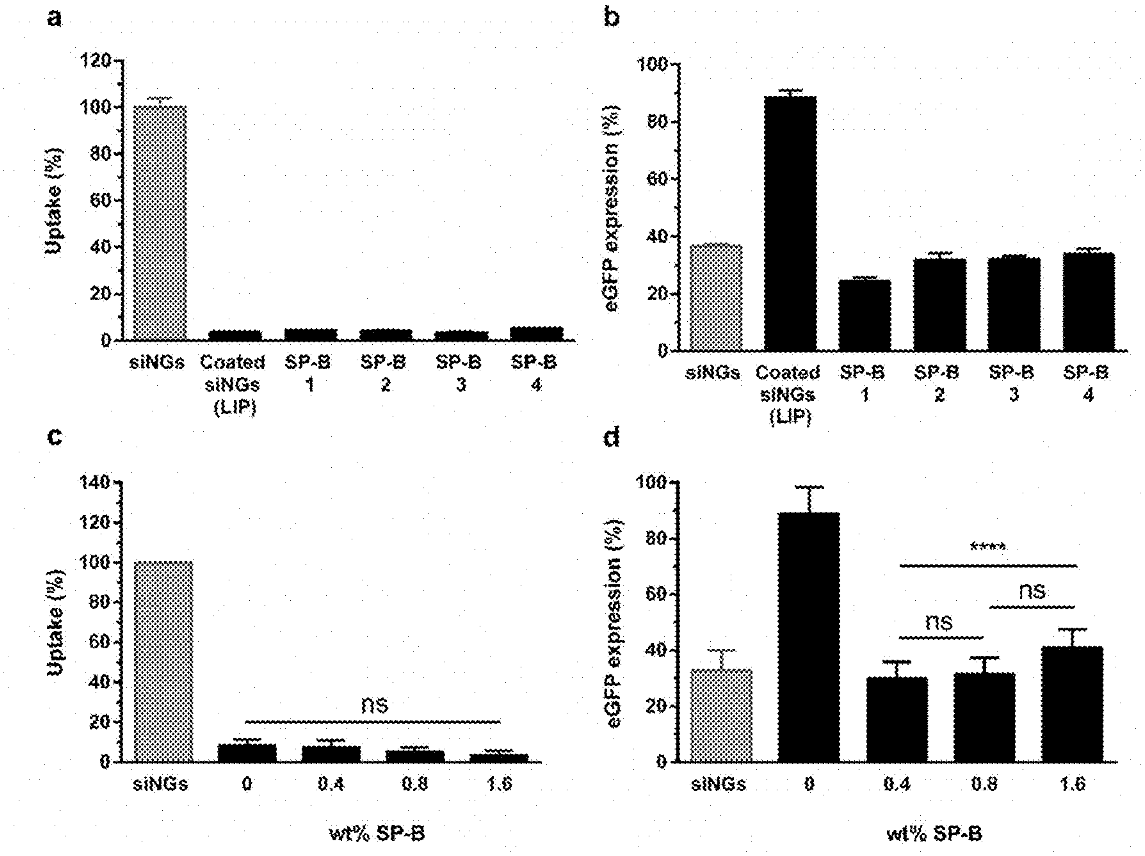
FIG. 6. Impact of SP-B source and concentration on the biological activity of the proteolipid coated siNGs. Evaluation of (a) cellular uptake and (b) gene silencing potential of coated siNGs incorporating SP-B isolated from different sources. The siNGs were layered with DOPC:eggPG (85:15 wt %). SP-B (0.4 wt %) isolated from 3 different native porcine lungs (SP-B 1; SP-B 2; SP-B 3) or isolated from Curosurf® (SP-B 4) was incorporated in the outer lipid layer (n=3, 1 independent repeat). Evaluation of (c) cellular uptake and (d) gene silencing potential of coated siNGs incorporating different concentrations of SP-B. The siNGs were layered with DOPC:eggPG (85:15 wt %) and SP-B isolated from native porcine lungs. In the uptake experiments, NGs were loaded with fluorescently labeled siRNA (siCy5), for which values of the coated formulations are shown relative to the maximal amount of particles taken up, i.e. for uncoated siNGs (100%). The eGFP expression was normalized to the expression of cells treated with control siRNA (siCTRL). All experiments were performed with a fixed NG concentration (30 μg/mL) and siRNA concentration (10 nM) (n=3, 4 independent repeats; ****$p \leq 0.0001$).

In previous experiments, we have observed a significant effect of SP-B on the siRNA delivery efficiency of our developed hybrid NP at low concentrations. For our first set of experiments, we opted to apply 0.4 wt % SP-B in the outer layer, based on the presence of SP-B in Curosurf®. In the following experiment, we have considered also higher concentrations of SP-B in the outer layer of the coated NPs, and evaluated the impact on the biological activity. In FIG. 6*c*, the cellular internalization data illustrate that the higher proportions of SP-B in the outer layer further diminish the uptake of coated siNGs by H1299_eGFP, while no marked differences on protein knockdown could be observed (FIG. 6*d*).

Evaluation of In Vivo TNFα Knockdown in Mouse Model of Acute Lung Injury (ALI)

Building further on the promising gene knockdown results with the SP-B proteolipid-coated nanogels, we next sought to obtain an in vivo proof-of-concept in a mouse model of acute lung injury (ALI). Naive BALB/c mice were prophylactically treated with the different NP formulations loaded with a TNFα targeting siRNA (siTNFα), 24 h prior to stimulation with LPS via tracheal aspiration. LPS exposure increased TNFα levels >20-fold compared to PBS control and NP administration in naive BALB/c mice. To quantify siRNA-induced TNFα knockdown, the TNFα levels in BAL of siTNFα treated mice were normalized to the TNFα levels measured for an identical formulation loaded with a non-active control siRNA (siCTRL).

Figure 7:
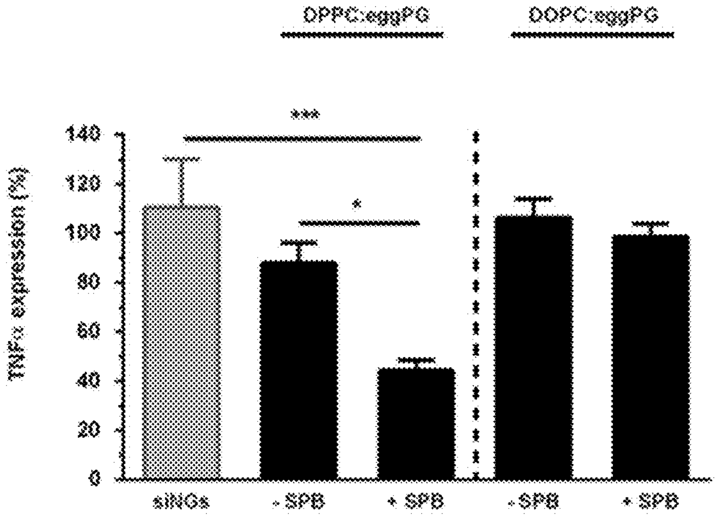
FIG. 7. Relative TNFα silencing in a murine acute lung injury (ALI) model. (a) Schematic representation of the executed experiment. (b) TNFα levels were quantified in BAL fluid extracted 24 h after LPS stimulation and thus 48 h after instillation of different siCTRL and siTNFα loaded NPs. The TNFα levels obtained with siTNFα loaded siNGs was normalized to the levels in BAL of mice that had received control siRNA (siCTRL). Mice were treated with a fixed NG dose (100 μg) loaded with 1 pmol siTNFα or siCTRL per μg NG (n=4, experiment performed once with 4 mice per group; *$p \leq 0.05$, ***$p \leq 0.001$).

The DPPC:eggPG coat was able to reduce the relative TNFα levels in BAL of LPS-exposed mice when supplemented with SP-B (FIG. 7).

Evaluation of Minimum Required SP-B Concentration and Replacement of SP-B by KL4

Figure 8:
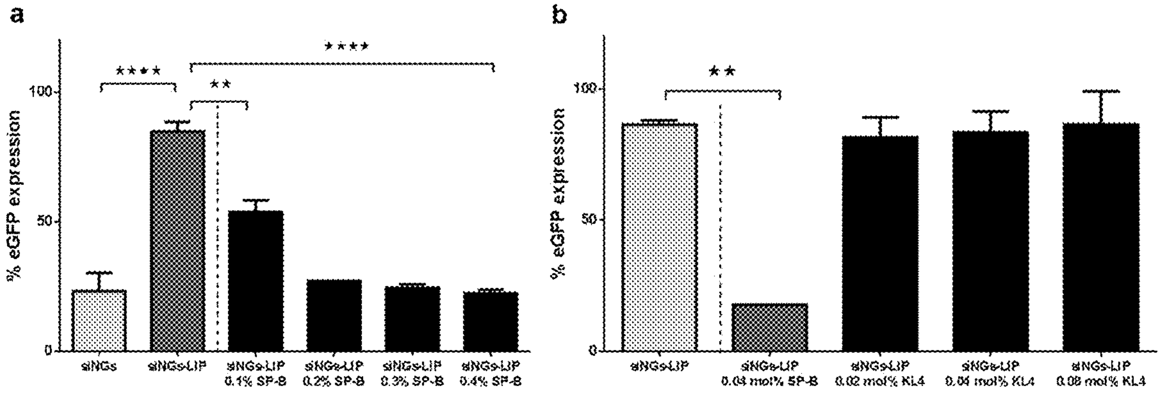
FIG. 8. (a) Evaluation of minimum required SP-B concentration within the proteolipid coating. Gene silencing potential of siNGs-LIP in H1299_eGFP cells was determined via flow cytometry. The siNGs were layered with DOPC:eggPG (85:15 wt %: coated siNGs (LIP)). In this LIP outer layer, SP-B in concentration range of 0.1-0.4 wt % was incorporated. (b) Biological activity of siNGs coated with synthetic surfactant peptide KL4 and lipids. The siNGs were layered with DOPC:eggPG (85:15 wt %: coated siNGs (LIP)). In this LIP outer layer, SP-B (0.04 mol %, corresponding to ~0.4 wt %) or the synthetic surfactant peptide KL4 in different concentrations were incorporated. Graphs contain data of two independent experiments (n=2, independent experiments; *$p \leq 0.05$, $p \leq 0.01$, *$p \leq 0.001$, ****$p \leq 0.0001$).

To assess the minimum required concentration of SP-B, siNGs were layered with a DOPC:eggPG (85:15 wt %) lipid coat incorporating varying concentrations of SP-B (0.1-0.4 wt %). Here, a clear concentration-dependent effect was observed. Already at a concentration of 0.1 wt % of SP-B, a significant enhancement in gene silencing was noted compared to the coated formulation devoid of SP-B. However, under the given experimental conditions, a 0.2 wt % of SP-B was required in the proteolipid coat to achieve optimal effects (FIG. 8*a*). Additionally, it was attempted to replace the SP-B by KL4, which is a synthetic cationic amphiphilic peptide that aims to mimic the most important physicochemical characteristics of SP-B. It is clear from our experiments, shown in FIG. 8*b*, that at the concentrations tested the KL4 peptide did not induce additional gene silencing and could not recapitulate the effects observed with native SP-B.

The Effect of Low SP-B Concentrations on siRNA Delivery Via Cationic Liposomes

Figure 9:
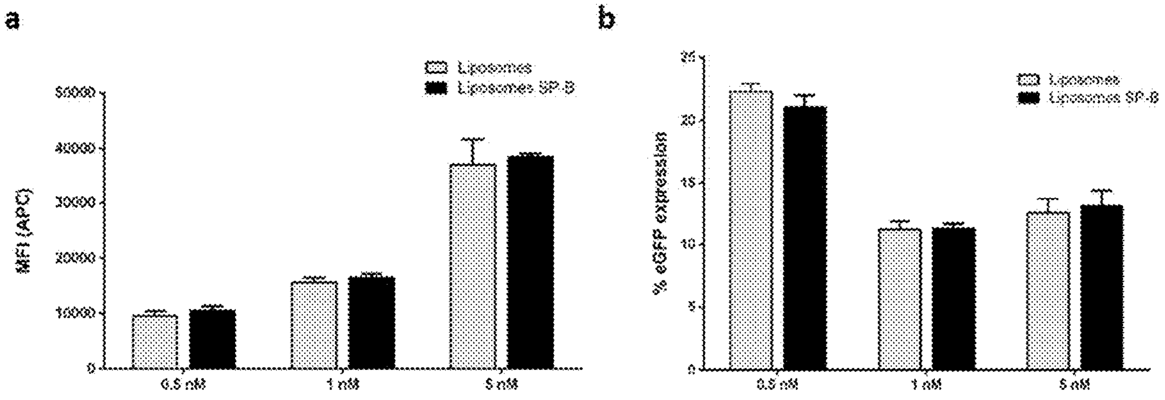
FIG. 9. (a) Cellular uptake and (b) eGFP gene silencing potential of DOTAP:DOPE (1:1 molar ratio) cationic liposomes, with and without supplementation of 0.4 wt % SP-B, in H1299_eGFP cells. Cellular uptake was determined by complexing Cy5-labeled siRNA in the liposomal formulation. Both uptake and gene silencing were quantified via flow cytometry. The eGFP expression of the cells treated with eGFP-targeting siRNA (siEGFP) was normalized to the expression of cells treated with control siRNA (siCTRL). Data are represented as means±SD (n=3, technical replicates).

To evaluate if the SP-B would equally improve siRNA delivery via cationic liposomes, we included SP-B (0.4 wt %) in cationic DOTAP:DOPE (1:1 molar ratio) liposomes. The inclusion of SP-B in the liposomal formulation did not impact the cellular uptake in the H1299eGFP cells (FIG. 9*a*). Although the liposomes complexing 0.5 nM of siRNA already induced a marked eGFP knockdown, doubling the dose of siRNA to 1 nM further improved the silencing effect. However, in contrast to our observations with the lipid-coated dextran nanogels, incorporating 0.4 wt % of SP-B in the cationic liposome formulation did not result in additional gene silencing, despite a comparable level of cellular internalization (FIG. 9*b*). These data suggest that SP-B is not able to promote cellular siRNA delivery when incorporated in a cationic liposomal formulation.

REFERENCES

De Backer, L., et al., The influence of natural pulmonary surfactant on the efficacy of siRNA-loaded dextran nanogels. Nanomedicine (London, United Kingdom), 2013. 8(10): p. 1625-1638.

De Backer, L., et al., Bio-inspired pulmonary surfactant-modified nanogels: A promising siRNA delivery system. J Control Release, 2015a. 206: p. 177-86.

De Backer, L., et al., Hybrid pulmonary surfactant-coated nanogels mediate efficient in vivo delivery of siRNA to murine alveolar macrophages. J Control Release, 2015b. 217: p. 53-63.

Blanco O, Pérez-Gil J. Biochemical and pharmacological differences between preparations of exogenous natural surfactant used to treat Respiratory Distress Syndrome: role of the different components in an efficient pulmonary surfactant. Eur J Pharmacol. 2007 Jul. 30; 568(1-3):1-15.

Olmeda B, et al., Structure-function correlations of pulmonary surfactant protein SP-B and the saposin-like family of proteins. Eur Biophys J. 2013 March; 42(2-3):209-22.

Olmeda B, et al., A model for the structure and mechanism of action of pulmonary surfactant protein B. FASEB J. 2015 October; 29(10):4236-47.

Parra, E. and J. Perez-Gil, Composition, structure and mechanical properties define performance of pulmonary surfactant membranes and films. Chemistry and Physics of Lipids, 2015. 185: p. 153-175.

Pérez-Gil, J., A. Cruz, and C. Casals, Solubility of Hydrophobic Surfactant Proteins in Organic-Solvent Water Mixtures—Structural Studies on Sp-B and Sp-C in Aqueous-Organic Solvents and Lipids. Biochimica Et Biophysica Acta, 1993. 1168(3): p. 261-270.

Rouser G., et al., Two dimensional thin layer chromatographic separation of polar lipids and determination of phospholipids by phosphorus analysis of spots, Lipids, 1970, 5: 494-496.

The invention claimed is:

1. A method for treating a pulmonary related disease in a subject in need thereof, the method comprising administering a composition to the subject, wherein the composition comprises a particle, the particle comprising one or more active agent(s) and a proteolipid composition, the proteolipid composition consisting of (a) a native surfactant-protein B (SP-B) or a peptide derived from the native SP-B, and wherein the peptide is not KL4, and (b) one or more lipids of which at least one is an anionic lipid; and whereby the composition delivers the one or more active agent(s) across cellular membranes in the subject.

2. The method according to claim 1, wherein the composition is locally administered to the subject.

3. The method according to claim 1, wherein the composition is administered by inhalation, by intranasal administration, by injection, as topical use, or incorporated within a slow- or delayed-release device.

4. The method according to claim 1, wherein the one or more lipids are phospholipids.

5. The method according to claim 4, wherein the phospholipids are selected from the group consisting of: 1,2-dioleoyl-sn-glycero-3-phosphocholine (DOPC), 1-palmitoyl-2-oleoyl-sn-glycero-3-phosphocholine (POPC), 1-stearoyl-2-oleoyl-sn-glycero-3-phosphocholine (SOPC), 1,2-dioleoyl-sn-glycero-3-phosphoethanolamine (DOPE), 1,2-dipalmitoyl-sn-glycero-3-phosphocholine (DPPC), 1,2-distearoyl-sn-glycero-3-phosphocholine (DSPC), 1,2-dimyristoyl-sn-glycero-3-phosphocholine (DMPC), 1,2-dila uroyl-sn-glycero-3-phosphocholine (DLPC), L-α-phosphatidylcholine ((egg)PC), L-α-phosphoethanolamine ((egg) PE), 1,2-dioleoyl-sn-glycero-3-phosphatidylglycerol (DOPG), L-α-phosphatidylglycerol ((egg)PG), 1,2-dioleoyl-sn-glycero-3-phosphatidic acid (DOPA), L-α-phosphatidic acid ((egg)PA), and combinations thereof.

6. The method according to claim 5, wherein the phospholipids are a combination of one or more zwitterionic phospholipids and one or more anionic phospholipids.

7. The method according to claim 6, wherein the phospholipids are a combination of DPPC:(egg)PG, a combination of DPPC:(egg)PA, a combination of DOPC:(egg)PG, or a combination of DOPC:(egg)PA.

8. The method according to claim 7, wherein the DPPC:(egg)PG, DPPC:(egg)PA, DOPC:(egg)PG or DOPC:(egg) PA has a ratio of about 85:15.

9. The method according to claim 1, wherein the native SP-B or peptide derived from the native SP-B is present at a weight ratio of about 0.1 wt % to about 5.0 wt % with respect to the complete proteolipid composition.

10. The method according to claim 1, wherein the native SP-B or peptide derived from the native SP-B is present at a weight ratio of about 0.4 wt % to about 1.6 wt % with respect to the complete proteolipid composition.

11. The method according to claim 1, wherein the particle is a dextran nanogel.

12. The method according to claim 1, wherein the particle is a cationic dextran nanogel.

13. The method according to claim 1, wherein one or more of the active agents is a nucleic acid.

14. The method according to claim 1, wherein one or more of the active agents is a nucleic acid selected from the group consisting of a small non-coding RNA and an RNA antisense oligonucleotide.

15. The method according to claim 1, wherein the particle further comprises a targeting ligand, an imaging agent, a fluorescent agent, a PEGylated lipid, or a functionalized lipid.

16. The method according to claim 1, wherein the composition is part of a pharmaceutical composition further comprising a pharmaceutically acceptable excipient, carrier and/or diluent.

17. The method according to claim 1, wherein the subject is a vertebrate, a domestic animal or a human being.

* * * * *

UNITED STATES PATENT AND TRADEMARK OFFICE

CERTIFICATE OF CORRECTION

PATENT NO. : 11,213,573 B2
APPLICATION NO. : 16/463946
DATED : January 4, 2022
INVENTOR(S) : Koen Raemdonck, Stefaan De Smedt and Jesus Perez-Gil It is certified that error appears in the above-identified patent and that said Letters Patent is hereby corrected as shown below:

On the Title Page

Item (57), abstract, Line(s) 10, delete "interfacing" and insert --interfering--, therefor.

Signed and Sealed this
Thirteenth Day of September, 2022

Katherine Kelly Vidal

Katherine Kelly Vidal
*Director of the United States Patent and Trademark Office*